US012295734B2

(12) United States Patent
Cho et al.

(10) Patent No.: US 12,295,734 B2
(45) Date of Patent: May 13, 2025

(54) WIRELESS ELECTROCARDIOGRAM MONITORING DEVICE

(71) Applicant: HUMANOO LAB, INC., Hwaseongi-si (KR)

(72) Inventors: Seong Je Cho, Suwon-si (KR); Seung Phil Jung, Seoul (KR)

(73) Assignee: HUMANOO LAB, INC., Hwaseongi-si (KR)

( * ) Notice: Subject to any disclaimer, the term of this patent is extended or adjusted under 35 U.S.C. 154(b) by 620 days.

(21) Appl. No.: 17/312,322

(22) PCT Filed: Dec. 18, 2019

(86) PCT No.: PCT/KR2019/018008
§ 371 (c)(1),
(2) Date: Jun. 9, 2021

(87) PCT Pub. No.: WO2020/130632
PCT Pub. Date: Jun. 25, 2020

(65) Prior Publication Data
US 2022/0022796 A1    Jan. 27, 2022

(30) Foreign Application Priority Data

Dec. 18, 2018  (KR) .................. 10-2018-0163803
Dec. 18, 2019  (KR) .................. 10-2019-0170133

(51) Int. Cl.
*A61B 5/282*      (2021.01)
*A61B 5/00*       (2006.01)
(Continued)

(52) U.S. Cl.
CPC .............. *A61B 5/282* (2021.01); *A61B 5/257* (2021.01); *A61B 5/274* (2021.01); *A61B 5/332* (2021.01);
(Continued)

(58) Field of Classification Search
CPC ......... A61B 5/282; A61B 5/257; A61B 5/274; A61B 5/332; A61B 5/6823; A61B 5/6826;
(Continued)

(56) References Cited

U.S. PATENT DOCUMENTS 5,511,553 A *  4/1996  Segalowitz ............ A61B 5/412
                                                     128/903
6,496,705 B1 * 12/2002  Ng .......................... A61N 1/05
                                                     600/509
(Continued)

FOREIGN PATENT DOCUMENTS

CN      102160786 A     8/2011
CN      204106001 U     1/2015
(Continued)

OTHER PUBLICATIONS

International Search Report, PCT/KR2019/018008, Korean Intellectual Property Office, 2 pages.
(Continued)

*Primary Examiner* — Catherine M Voorhees
(74) *Attorney, Agent, or Firm* — Faegre Drinker Biddle & Reath LLP

(57) ABSTRACT

Provided is a wireless electrocardiogram monitoring device comprising: a patch part including a plurality of electrodes; and a module part detachably coupled to the patch part and capable of wireless communication with an external device, wherein the patch part comprises: a downward patch part formed at the bottom surface to be attached to the human body while some of the plurality of electrodes are exposed from the bottom surface; and an upward patch part disposed at the top surface opposite to the bottom surface while the others of the plurality of electrodes are exposed from the top surface.

7 Claims, 5 Drawing Sheets

(51) Int. Cl.
    *A61B 5/257*     (2021.01)
    *A61B 5/274*     (2021.01)
    *A61B 5/332*     (2021.01)
    *A61N 1/04*     (2006.01)

(52) U.S. Cl.
    CPC .......... *A61B 5/6823* (2013.01); *A61B 5/6826* (2013.01); *A61N 1/0492* (2013.01); *A61B 2560/0214* (2013.01); *A61B 2560/0443* (2013.01)

(58) Field of Classification Search
    CPC .... A61B 2560/0214; A61B 2560/0443; A61B 5/002; A61B 2560/045; A61B 2562/164; A61N 1/0492
    See application file for complete search history.

(56) References Cited

U.S. PATENT DOCUMENTS

| | | | | |
|---|---|---|---|---|
| 7,206,630 | B1* | 4/2007 | Tarler | A61B 5/398 |
| | | | | 600/509 |
| 7,647,093 | B2* | 1/2010 | Bojovic | A61B 5/0006 |
| | | | | 600/512 |
| 2002/0026114 | A1* | 2/2002 | Nissila | A61B 5/0245 |
| | | | | 600/384 |
| 2006/0217620 | A1 | 9/2006 | Bojovic et al. | |
| 2007/0149887 | A1* | 6/2007 | Hwang | A61B 5/257 |
| | | | | 600/509 |
| 2009/0182241 | A1* | 7/2009 | Maruccio | A61B 5/282 |
| | | | | 600/509 |
| 2010/0049028 | A1 | 2/2010 | Shin et al. | |
| 2012/0306662 | A1* | 12/2012 | Vosch | H04Q 9/00 |
| | | | | 340/870.07 |
| 2016/0192716 | A1* | 7/2016 | Lee | A61B 5/01 |
| | | | | 2/243.1 |
| 2016/0296132 | A1* | 10/2016 | Bojovic | G16H 50/20 |
| 2017/0100046 | A1 | 4/2017 | Roh et al. | |
| 2017/0150891 | A1 | 6/2017 | Tsuchimoto et al. | |
| 2018/0000415 | A1 | 1/2018 | Gupta et al. | |
| 2019/0044362 | A1* | 2/2019 | Beyer | H02J 7/00714 |
| 2021/0177291 | A1* | 6/2021 | Bhagat | A61B 5/7445 |

FOREIGN PATENT DOCUMENTS

| | | |
|---|---|---|
| CN | 105722455 A | 6/2016 |
| CN | 106913330 A | 7/2017 |
| CN | 207768388 U | 8/2018 |
| JP | 6252682 B2 | 12/2017 |
| KR | 20060116190 A | 11/2006 |
| KR | 20070043124 A | 4/2007 |
| KR | 20170042595 A | 4/2017 |
| KR | 1020170041595 A | 4/2017 |
| KR | 20170128859 A | 11/2017 |
| WO | 2005018447 A1 | 3/2005 |

OTHER PUBLICATIONS

European Patent Office; European Search Report; EP Application No. 19898226.6; 7 pages; dated Dec. 12, 2022.

China National Intellectual Property Administration; Chinese Office Action; Chinese Application No. 201980077025.2; 13 pages; dated Nov. 30, 2023.

China National Intellectual Property Administration; Chinese Second Office Action with English translation; Chinese Application No. 201980077025.2; 43 pages; dated May 31, 2024.

China National Intellectual Property Administration; Chinese Decision of Rejection with English translation; Chinese Application No. 201980077025.2; 53 pages; dated Oct. 23, 2024.

\* cited by examiner

WIRELESS ELECTROCARDIOGRAM MONITORING DEVICE

CROSS-REFERENCE TO RELATED APPLICATIONS

The present application is a national stage application of International (PCT) Patent Application Serial No. PCT/KR2019/018008, filed on Dec. 18, 2019, which claims priority to KR 10-2019-0170133, filed on Dec. 18, 2019, and KR 10-2018-0163803, filed on Dec. 18, 2018, the complete disclosures of which are expressly incorporated by reference herein.

TECHNICAL FIELD

The present invention relates to a wireless electrocardiogram monitoring device, and more particularly, to a wireless electrocardiogram monitoring device configured to check health and cardiac conditions.

BACKGROUND ART

The term electrocardiogram refers to an action current according to contraction or dilatation of myocardium. In detail, action potential generated when the myocardium contracts or relaxes may generate a current which spreads from a heart to a whole body. The current may generate a potential difference according to a body position. In addition, the potential difference may be detected through a surface electrode attached to skin of a human body. Accordingly, the electrocardiogram may be measured by attaching an electrode to a surface of a body.

Since the electrocardiogram is measurable through a non-invasive test with no pain or side effect to a testee, the electrocardiogram is often used clinically. Also, the electrocardiogram is used basically in order to check whether a cardiac abnormality is present and to diagnose cardiac diseases such as angina, myocardial infraction, arrhythmia, and the like.

In addition, in order to diagnose a variety of such cardiac diseases, electrocardiograms of twelve channels are measured. As an example, in conventional techniques, electrocardiograms of twelve channels are measured using information obtained through ten electrodes or leads.

Here, when a device for measuring the electrocardiogram is connected to electrodes attached to a human body through wires, there is a problem that inconvenience is caused to a user by complicated wires.

In addition, as a conventional technique, an electrocardiogram monitoring device provided as a patch type attached to a human chest (hereinafter, referred to as a patch-type electrocardiogram monitoring device) is disclosed. In detail, the patch-type electrocardiogram monitoring device may be formed to have a cloth type or any patch type detachably attached to a chest so as to attach all electrodes to a human body in one attempt. Also, the patch-type electrocardiogram monitoring device may observe an electrocardiogram in wireless connection with another electrical device.

However, in the conventional patch-type electrocardiogram monitoring device, a variety of the following problems occur due to a limitation in a size of a patch or a trade off relation.

First, since the conventional patch-type electrocardiogram monitoring device includes a small number of electrodes to be attached to a human body, there is a problem that only a 1-channel or 3-channel electrocardiogram is measured. In this case, there is a disadvantage that only arrhythmia is measurable and a variety of electrocardiograms are not analyzable. For example, since it is impossible to check whether a significant cardiac abnormality such as a ST-elevation myocardial infraction (STEMI) and the like occurs using the conventional patch-type electrocardiogram monitoring device, there is a problem that utilization thereof decreases.

In addition, in order to reduce a size as well as increase availability, in the conventional patch-type electrocardiogram monitoring device, there is disclosed a technique of changing limb leads RA, LA, RL, and LL to connect by wire in addition to electrodes attached to a human chest (or thorax) or of changing attachment positions of some electrodes of the limb leads to upper arm parts (near shoulders).

Meanwhile, electrodes RA and LA attached to both arms of a human body among the limb leads are essential signal elements to implement 12-channel electrocardiograms.

However, in the conventional patch-type electrocardiogram monitoring device, since the electrodes RA and LA attached to the arms are located at the upper arm parts, particularly, near the shoulders, when the electrodes are attached to a right hand and a left hand, a problem that signal intensity further decreases, a problem that noise occurs due to compulsory amplification, and a problem that an electrocardiogram signal becomes inaccurate occur. Eventually, the conventional patch-type electrocardiogram monitoring device has a lower reliability in comparison to wire electrocardiogram monitoring devices.

In addition, it is difficult to individually use the conventional patch-type electrocardiogram monitoring device due to lack of a means capable of guiding an accurate attachment position of an electrode.

Related art document information is as follows.

RELATED ART DOCUMENTS

Patent Documents

Patent Document 1: KR 10-2017-0041595 A, Wearable and wireless 12-channel electrocardiograph system
Patent Document 2: KR 10-2009-0102943 A, Real-time electrocardiogram monitoring system and method, patch-type electrocardiograph, and telecommunication apparatus

DISCLOSURE

Technical Problem

The present invention is directed to providing a wireless electrocardiogram monitoring device configured to remedy problems of the above-described conventional electrocardiogram monitoring device.

The present invention is also directed to providing a wireless electrocardiogram monitoring device in which an electrode connected to a human hand or finger is integrally formed with an electrode attached to a human chest.

The present invention is also directed to providing a wireless electrocardiogram monitoring device in which an electrode connected to a hand or a finger is easily installed and which is easily utilizable even for a person losing his or her consciousness or having difficulty in moving his or her arms.

The present invention is also directed to providing a miniaturized patch-type wireless electrocardiogram monitoring device detachably attachable to a human body at once.

Technical Solution

One aspect of the present invention provides a wireless electrocardiogram monitoring device including a patch portion including a plurality of electrodes to be detached or attached to a human body in one attempt; and a module portion separably coupled to the patch portion and configured to perform transmission/reception of information, processing of signals, and wireless communication. Here, the patch portion includes a downward patch portion formed on a bottom surface attached to the human body and including some of the plurality of electrodes to be exposed through the bottom surface; and an upward patch portion located on an outer surface exposed outward and including other of the plurality of electrodes to be exposed through the outer surface.

The upward patch portion may include an upward contact portion protruding upward from the outer surface; and an upward electrode portion extending toward a bottom of the upward contact portion and electrically connected to the module portion.

The upward contact portion may be formed to have a thimble shape or a protrusion shape to allow a finger to be inserted thereinto.

A plurality of such upward contact portions may be provided and may be formed to have the same height.

The upward contact portion may be formed to have an engraved shape.

The downward patch portion may include a downward adhesive portion formed of a skin-adhesive material to be attachable to a chest of the human body, a downward contact portion located to be coplanar with the downward adhesive portion and coming into contact with the human body, and a downward electrode portion extending upward from the downward contact portion electrically connected to the module portion.

The downward patch portion may include first to sixth electrodes C1 to C6 attached to first to sixth electrode positions V1 to V6 which are positions defined on the chest to measure an electrocardiogram of the human body.

The upward patch portion may be located on a virtual straight line which vertically and equally divides a horizontal line connecting the first electrode C1 and the second electrode C2. Accordingly, the upward patch portion may have an advantage of being provided as a position conveniently touched by a hand or finger of the user.

The upward patch portion may include a fixing portion fixed to the top surface of the patch portion and including an upward electrode portion electrically connected to the module portion, and a separation portion separably coupled to the fixing portion and including an upward contact portion coming into contact with the human body.

The fixing portion may further include an upward installation portion configured to provide a coupling force to the separation portion.

The separation portion may further include an upward electrode guide connected to a bottom of the upward contact portion and configured to guide electrical connection by coming into contact with the upward electrode portion; and an upward installation portion located to correspond to the upward installation portion and detachably attached to the upward installation portion.

The fixing portion and the separation portion may be formed as one pair to be coupled using any one of a Velcro type, a magnet type, and a snap-button type. Accordingly, there may be provided an advantage of stably coupling the upward patch portion which is separably provided.

The plurality of electrodes may be provided as nine or ten electrodes, and the upward patch portion may include two electrodes among the nine or ten electrodes to be attached to both hands or fingers of the human body.

The patch portion may further include a module mounting portion electrically connected to the plurality of electrodes and on which the module portion is installed. Also, the module mounting portion may include an electrical connection device electrically connected to the plurality of electrodes through a printed circuit; and a magnet located at a central part.

The electrical connection devices may include pogo-pins.

The module portion may include a module magnet located on a bottom surface to be coupled to the magnet and a module pogo-pin electrically connected to the pogo-pin.

The module portion may include a communication module configured to perform wireless communication; a battery configured to provide power; a universal serial bus (USB) port configured to charge the battery; and a switch configured to control turning the power on or off.

The wireless electrocardiogram monitoring device may further include a smart device communicatively connected to the module portion to receive size information of the patch portion and configured to guide an attachment position of the patch portion using an augmented screen on a captured image of the human body.

Advantageous Effects

According to the present invention, a size of a patch-type electrocardiogram monitoring device may be minimized to be easily attached to or detached from a human body. Simultaneously, there is an advantage that limb leads are integrally formed and an additional wired connection is unnecessary. In addition, since it is possible to remedy problems such as a signal loss, inaccuracy, and noise according to measurement positions of limb leads in the above-described conventional technique, availability and reliability may be further improved than conventional wireless electrocardiogram monitoring devices.

Also, since some electrodes are provided upward on a patch portion detachably attached to a chest of a human body to mount the electrodes on hands or fingers of the human body, a current reaching from a heart to the hands via shoulders and arms may be detected so that stability of an electrocardiogram signal may be increased further than the conventional device.

Also, since the electrocardiogram monitoring device is provided as a patch type easily attachable to or detachable from the human body, user convenience may be increased.

Also, since all electrodes attached to the human body and a module electrically connected to the electrodes to measure electrocardiograms are integrally provided, complicated wires are unnecessary, carrying is easy, and installation is simple.

Also, the electrodes attached to the hands or fingers are located above the patch portion and the electrodes attached to the chest of the human body are located below the patch portion so that accuracy of the electrocardiogram signal may be increased and the device may be compact.

Also, since a finger patch attached to the hand or finger is included to be detachably attachable to the electrode formed on a top of the patch portion, a person losing his or her consciousness or having difficulty in moving his or her arms may also easily use the wireless electrocardiogram monitoring device.

Also, since it is possible to interoperate with another smart device through a module capable of performing wireless communication, electrocardiography and diagnosis may be received at home so that availability may be increased.

Also, since a precise installation position is guided using a smart device, it is possible to decrease a level of difficulty in domestic or personal installation of the electrocardiogram monitoring device.

DESCRIPTION OF DRAWINGS

FIG. 11 is a plan view illustrating a patch portion according to another embodiment of the present invention.

FIG. 12 is a front view illustrating a module portion according to another embodiment of the present invention.

MODES OF THE INVENTION

Figure 1:
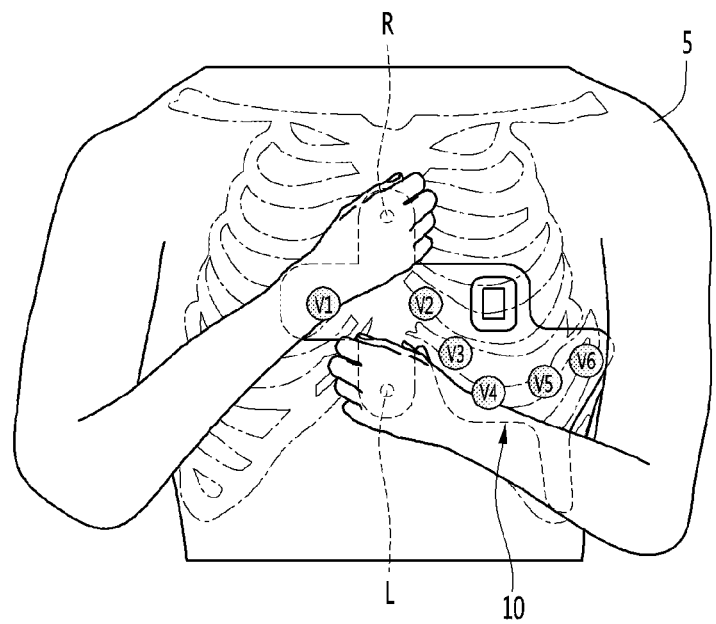
FIG. 1 is a view illustrating an example of using a wireless electrocardiogram monitoring device according to one embodiment of the present invention.

Hereinafter, some embodiments of the present invention will be described with reference to exemplary drawings. While reference numerals are given to components of each drawing, it should be noted that although shown in different drawings, like components will be referred to as like reference numerals if possible. Also, in a description of the embodiments of the present invention, a detailed description of well-known components or functions of the related art will be omitted when it is deemed to obscure understanding of the embodiments of the present invention.

Also, when it is stated that one component is "connected," "coupled," or "joined" to another component, it should be understood that the one component may be directly connected or coupled to the other component but still another component may be interposed between the components to be "connected," "coupled," or "joined" thereto.

FIG. 1 is a view illustrating an example of using a wireless electrocardiogram monitoring device according to one embodiment of the present invention.

Referring to FIG. 1, a wireless electrocardiogram monitoring device 10 according to one embodiment of the present invention may measure electrocardiograms of twelve channels using nine or ten electrodes. Also, the wireless electrocardiogram monitoring device 10 may be formed so as to attach or detach the nine or ten electrodes to or from a human body 5 at once.

That is, the wireless electrocardiogram monitoring device 10 may include one sheet or patch detachably attached to the human body 5.

The wireless electrocardiogram monitoring device 10 may provide information such as signals, an average heart rate, a maximum heart rate, a minimum heart rate, an instantaneous heart rate, and the like of the electrocardiograms of the twelve channels in real time.

Figure 7:
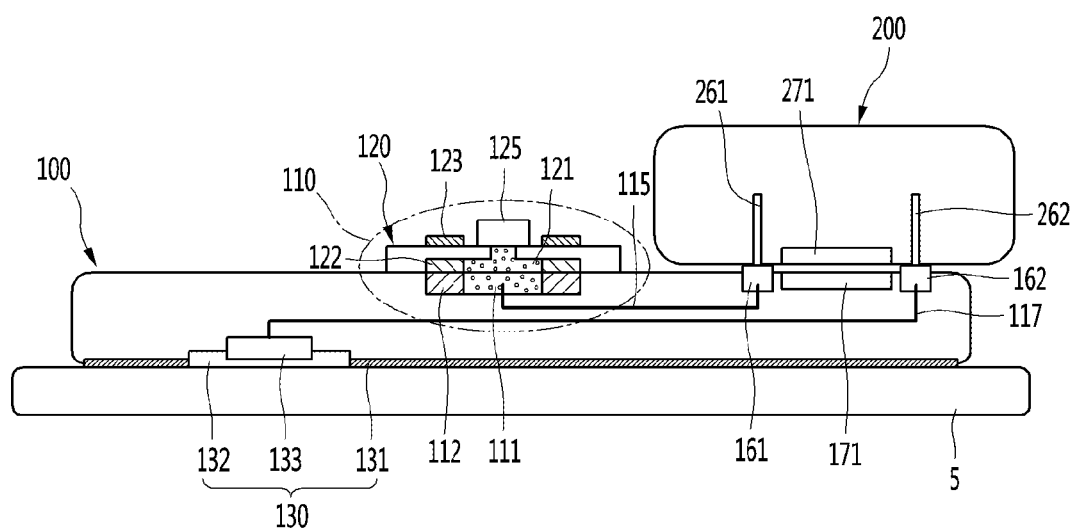
FIG. 7 is a longitudinal cross-sectional view exemplarily illustrating a structure of the wireless electrocardiogram monitoring device according to one embodiment of the present invention.

Here, referring to FIG. 7, the wireless electrocardiogram monitoring device 10 may include a patch portion 100 detachably attached to the human body 5 and a module portion 200 separably coupled to the patch portion 100.

The patch portion 100 may be formed as one sheet or patch.

Also, the patch portion 100 may include nine or ten electrodes detachably attached to the human body 5. Accordingly, the nine or ten electrodes may be attached to or detached from the human body 5 in one attempt by the patch portion 100.

Six electrodes of the nine or ten electrodes included in the patch portion 100 may be attached to a chest of the human body 5.

In detail, six electrodes C1 to C6 attached to the chest may be attached or located to correspond to a first electrode position V1, a second electrode position V2, a third electrode position V3, a fourth electrode position V4, a fifth electrode position V5, and a sixth electrode position V6 respectively on the basis of the human body 5 shown in FIG. 1.

Generally, the first electrode position V1 may be defined to be beside a right sternum of a fourth intercostal space. The second electrode position V2 may be defined to be beside a left sternum of the fourth intercostals space. The fourth electrode position V4 may be defined to be a central clavicular line of a fifth intercostal space. The third electrode position V3 may be defined to be a relative position between the second electrode position V2 and the fourth electrode position V4. The fifth electrode position may be spaced apart from and horizontally parallel to the fourth electrode position V4 in a direction toward an armpit and may be defined to be a position on a left side of the armpit. The sixth electrode position V6 may be located to be spaced apart from and horizontally parallel to the fourth electrode position V4 or the fifth electrode position V5 and may be defined to be a position at a middle armpit line part.

The first to sixth electrodes C1 to C6 which will be described below may be correspondingly attached to the first to sixth electrode positions V1 to V6, respectively.

The first to sixth electrode positions V1 to V6 are not absolute positions and may have a slight difference according to a shape or size of the human body 5.

Meanwhile, one electrode of the nine electrodes included in the patch portion 100 may be attached to a left leg or a lower part of a rib closest to the left leg.

Here, the electrode attached to the left leg or the lower part of the left rib may be referred to as a furcating electrode F which may be attached lower than the fourth electrode position V4.

Also, when the patch portion 100 includes ten electrodes, one electrode may be attached to the left leg and another electrode may be attached to a right leg or a lower part of a rib closest to the right leg. However, the electrode attached to the right leg or the lower part of the rib closest to the right leg may be omitted.

Accordingly, the embodiment of the present invention will be described below in detail on the basis of a case in which the patch portion 100 includes nine electrodes.

Two other electrodes among the nine electrodes included in the patch portion 100 may be attached to a left hand and a right hand, respectively.

Here, the electrode attached to the left hand is referred to as a left electrode L and the electrode attached to the right hand is referred to as a right electrode R.

The right electrode R may come into contact with any one finger of the right hand of the human body 5. Also, the left electrode L may come into contact with any one finger of the left hand of the human body 5.

The right electrode R and the left electrode L may be formed on a top surface of the patch portion 100 to be exposed. Also, the first to sixth electrodes C1 to C6 and the furcating electrode F may be formed on a bottom surface of the patch portion 100 to be exposed.

That is, in the patch portion 100, the right electrode R and the left electrode L may be disposed toward a direction opposite to the first to sixth electrodes C1 to C6 and the furcating electrode F.

In addition, since the right electrode R and the left electrode L are provided integrally with the first to sixth electrodes C1 to C6 and the furcating electrode F on one sheet or patch, a signal provided from the hand or finger of the human body 5 has a feature obtainable from the integrated patch portion detachably attached to the chest.

Accordingly, when a user places a left hand and a right hand on a central part of the wireless electrocardiogram monitoring device 10 attached to a user's chest, the wireless electrocardiogram monitoring device 10 may measure electrocardiograms of twelve channels by sensing voltages of the first to sixth electrodes C1 to C6, the furcating electrode F, the left electrode L, and the right electrode R. Accordingly, since it is possible to minimize the size of the patch portion 100 as well as obtain a voltage or current from the hand via a shoulder and an arm from a cardiac action, stability and reliability of a signal may be improved.

A related structure of the wireless electrocardiogram monitoring device 10 will be described in detail.

A principle of measuring the electrocardiograms of the twelve channels by sensing voltages of the first to sixth electrodes C1 to C6, the furcating electrode F, the left electrode L, and the right electrode R will be described.

The 12 channels may include channel I, channel II, channel III, channel V1, channel V2, channel V3, channel V4, channel V5, channel V6, channel aVR, channel aVL, and channel aVF.

The channel I is obtained by a difference between the voltage of the left electrode L and the voltage of the right electrode R. The channel II is obtained by a difference between the voltage of the furcating electrode F and the voltage of the right electrode R. Also, the channel III is obtained by a difference between the channel II and the channel I.

In addition, the channel V1 is a value obtained by subtracting a mean value of the voltages of the right electrode R, the left electrode L, and the furcating electrode F from the voltage of the first electrode C1. The channel V2 is a value obtained by subtracting the mean value of the voltages of the right electrode R, the left electrode L, and the furcating electrode F from the voltage of the second electrode C2. The channel V3 is a value obtained by subtracting the mean value of the voltages of the right electrode R, the left electrode L, and the furcating electrode F from the voltage of the third electrode C3. The channel V4 is a value obtained by subtracting the mean value of the voltages of the right electrode R, the left electrode L, and the furcating electrode F from the voltage of the fourth electrode C4. The channel V5 is a value obtained by subtracting the mean value of the voltages of the right electrode R, the left electrode L, and the furcating electrode F from the voltage of the fifth electrode C5. The channel V6 is a value obtained by subtracting the mean value of the voltages of the right electrode R, the left electrode L, and the furcating electrode F from the voltage of the sixth electrode C6.

Also, the channel aVR is a value obtained by dividing a sum of the channel I and the channel II by two. The channel aVL is a value obtained by dividing a difference between the channel I and the channel II by two. The channel aVF is a value obtained by dividing a difference between the channel II and the channel I by two.

Accordingly, the wireless electrocardiogram monitoring device 10 may measure the electrocardiograms of the twelve channels in real time using voltage information provided from the nine electrodes.

Meanwhile, the principle of measuring the electrocardiograms of the twelve channels may be processed by the module portion 200.

The module portion 200 may be electrically connected to the above nine electrodes, that is, the first to sixth electrodes C1 to C6, the furcating electrode F, the left electrode L, and the right electrode R.

In addition, the module portion 200 may measure, process, store, transmit, and display the electrocardiograms of the twelve channels from the voltage information sensed by the nine electrodes.

Also, the module portion 200 may be separably coupled to the patch portion 100. Accordingly, the user may simply separate the module portion 200 from the patch portion 100 and charge the module portion 200 with power.

Figure 2:
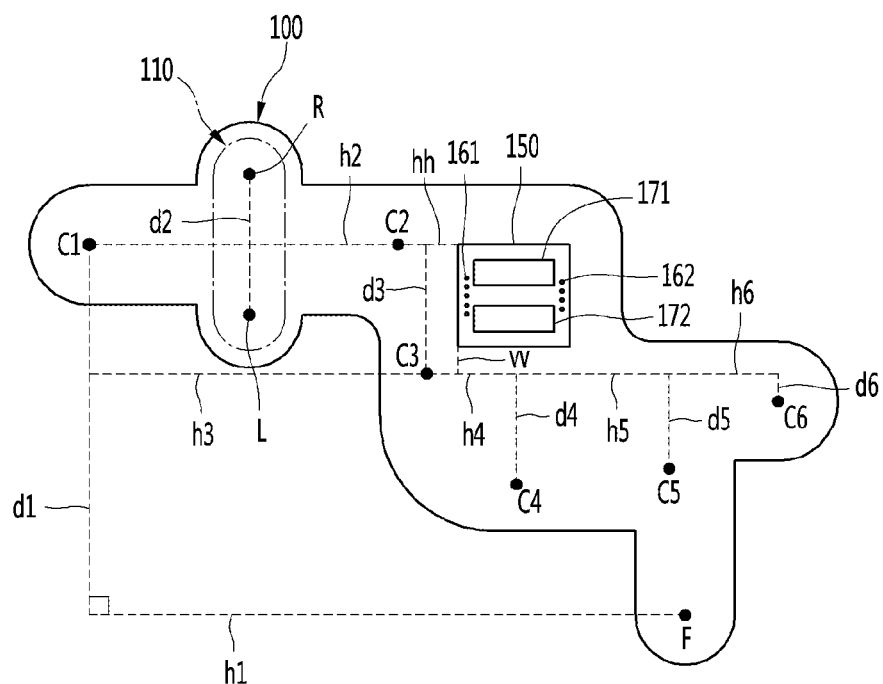
FIG. 2 is a view illustrating a patch portion according to one embodiment of the present invention.

FIG. 2 is a view illustrating the patch portion according to one embodiment of the present invention.

Referring to FIG. 2, the patch portion 100 may include a plurality of electrodes detachably attachable to the human body 5. As an example, the patch portion 100 covers the plurality of electrodes and may be formed as an adhesive sheet having a hydrocolloid material.

The plurality of electrodes may be attached to the skin of the human body 5 so as to measure electrocardiograms.

In the wireless electrocardiogram monitoring device 10 according to one embodiment of the present invention, the plurality of electrodes may be nine electrodes as described above. That is, the patch portion 100 may be formed as an integrated sheet or patch surrounding the nine electrodes while being spaced outward at a certain distance therefrom.

In detail, the patch portion 100 may include the first to sixth electrodes C1 to C6, the furcating electrode F, the right electrode R, and the left electrode L.

The first to sixth electrodes C1 to C6 may be attached to the chest of the human body 5 to correspond to the first to sixth electrode positions V1 to V6, respectively.

The furcating electrode F may be attached lower than the fourth electrode C4 of the human body 5.

The right electrode R and the left electrode L may be attached to the right hand and the left hand of the human body 5, respectively.

The patch portion 100 may include the bottom surface which comes into contact with or is attached to the chest of the human body and the top surface in a direction opposite to the bottom surface, that is, in a direction exposed outward.

The first to sixth electrodes C1 to C6 and the furcating electrode F may be formed on the bottom surface of the patch portion 100. Accordingly, when the bottom surface of the patch portion 100 is attached to the human body 5, the first to sixth electrodes C1 to C6 and the furcating electrode F may come into contact with the human body 5.

Also, the right electrode R and the left electrode L may be formed on the top surface of the patch portion 100.

An area or size of the patch portion 100 may be determined according to positions of the nine electrodes. Hereinafter, as one embodiment, relative positions of the nine electrodes will be described with detailed numerical values.

The numerical values which will be described below may be values set on the basis of an average height, chest size, and weight of an adult. Accordingly, in the wireless electrocardiogram monitoring device 10, a variety of sizes of the patch portion 100 may be manufactured for a child, youth, adult, and the like by designing relative numerical values of the nine electrodes to be changed.

The furcating electrode F may be located below the first electrode C1 by a first vertical distance d1 and rightward therefrom by a first horizontal distance h1. As an example, the first vertical distance d1 may be set to be 120.5 mm and the first horizontal distance h1 may be set to be 203.5 mm.

The second electrode C2 may be located rightward from the first electrode C1 by a second horizontal distance h2. That is, the second electrode C2 may be located on one straight line parallel to the first electrode C1. As an example, the second horizontal distance h2 may be set to be 102 mm.

The right electrode R and the left electrode L may be located on a vertical line dividing a distance between the first electrode C1 and the second electrode C2 equally.

That is, the right electrode R may be located rightward from the first electrode C1 by half the second horizontal distance h2 and upward therefrom by a second vertical distance d2. Also, the left electrode L may be located rightward from the first electrode C1 by half the second horizontal distance h2 and downward therefrom by the second vertical distance d2. As an example, the second vertical distance d2 may be set to be 25 mm.

The third electrode C3 may be located rightward from the first electrode C1 by a third horizontal distance h3 and downward therefrom by a third vertical distance d3. As an example, the third horizontal distance h3 may be set to be 111.8 mm and the third vertical distance d3 may be set to be 44.4 mm.

The fourth electrode C4 may be located rightward from the third electrode C3 by a fourth horizontal distance h4 and downward therefrom by a fourth vertical distance d4. As an example, the fourth horizontal distance h4 may be set to be 31 mm and the fourth vertical distance d4 may be set to be 34.9 mm.

The fifth electrode C5 may be located rightward from the third electrode C3 by a sum of the fourth horizontal distance h4 and a fifth horizontal distance h5 and downward therefrom by a fifth vertical distance d5. As an example, the fifth horizontal distance h5 may be set to be 52.2 mm, and the fifth vertical distance d5 may be set to be 30.2 mm.

Here, the fifth electrode C5 may be located rightward from the fourth electrode C4 by the fifth horizontal distance h5.

The sixth electrode C6 may be located rightward from the third electrode C3 by a sum of the fourth horizontal distance h4, the fifth horizontal distance h5, and a sixth horizontal distance h6 and downward therefrom by a sixth vertical distance d6. As an example, the sixth horizontal distance h6 may be set to be 38.7 mm and the sixth vertical distance d6 may be set to be 11 mm.

The patch portion 100 may further include a module mounting portion 150 to which the module portion 200 is separably coupled.

The module mounting portion 150 may be formed on the top surface of the patch portion 100 to be exposed outward.

The module mounting portion 150 may be located rightward from the third electrode C3 by a horizontal separation distance hh and upward therefrom by a vertical separation distance vv. As an example, the horizontal separation distance hh may be set to be 13.5 mm and the vertical separation distance vv may be set to be 11.4 mm.

The module mounting portion 150 may be formed to have a shape and a size corresponding to a bottom surface of the module portion 200. As an example, the module mounting portion 150 may be provided as a thin quadrangular plate.

The module mounting portion 150 may include magnets 171 and 172 configured to guide the module portion 200 to be simply and stably coupled.

The magnets 171 and 172 may be located at a central part of the module mounting portion 150.

Also, a plurality of such magnets 171 and 172 may be provided.

In detail, the magnets 171 and 172 may include a first magnet 171 and a second magnet 172. The first magnet 171 and the second magnet 172 may be located to be spaced at a certain vertical distance apart from each other.

Also, the second magnet 172 may be located below the first magnet 171.

The magnets 171 and 172 are magnetic bodies. Accordingly, the magnets 171 and 172 may provide a separable coupling force using a magnetic force.

In detail, the magnets 171 and 172 may be coupled to module magnets 271 and 272 provided on a bottom of the module portion 200. Accordingly, the magnets 171 and 172 and the module magnets 271 and 272 of the module portion 200 may be located to correspond to each other.

Also, the magnets 171 and 172 and the module magnets 271 and 272 may be formed so as to apply attraction to each other.

The module mounting portion 150 may further include electrical connection devices 161 and 162 electrically connected to the plurality of electrodes.

The electrical connection devices 161 and 162 may include pogo-pins. Hereinafter, for a detailed description, a case in which the electrical connection devices 161 and 162 are provided as pogo-pins will be described as a reference. Accordingly, hereinafter, the electrical connection devices 161 and 162 will be referred to as pogo-pins.

A plurality of such pogo-pins 161 and 162 may be provided. As an example, the number of the pogo-pins 161 and 162 may be nine. Here, the plurality of pogo-pins 161 and 162 may be electrically connected to the nine electrodes, respectively.

That is, the plurality of pogo-pins 161 and 162 may be electrically connected to the first to sixth electrodes C1 to C6, the furcating electrode F, the right electrode R, and the left electrode L, respectively. As an example, the pogo-pins 161 and 162 may be connected to at least any one of the nine electrodes through a printed circuit type.

The pogo-pins 161 and 162 may include a first pogo-pin 161 located to be spaced apart from the magnets 171 and 172 in one direction and a second pogo-pin 162 located to be spaced apart from the magnets 171 and 172 in another direction.

The first pogo-pin 161 may include five pogo-pins. Here, the five pogo-pins 161 may be disposed in a row.

The second pogo-pin 162 may include four pogo-pins. Here, the four pogo-pins may be disposed in a row.

Figure 3:
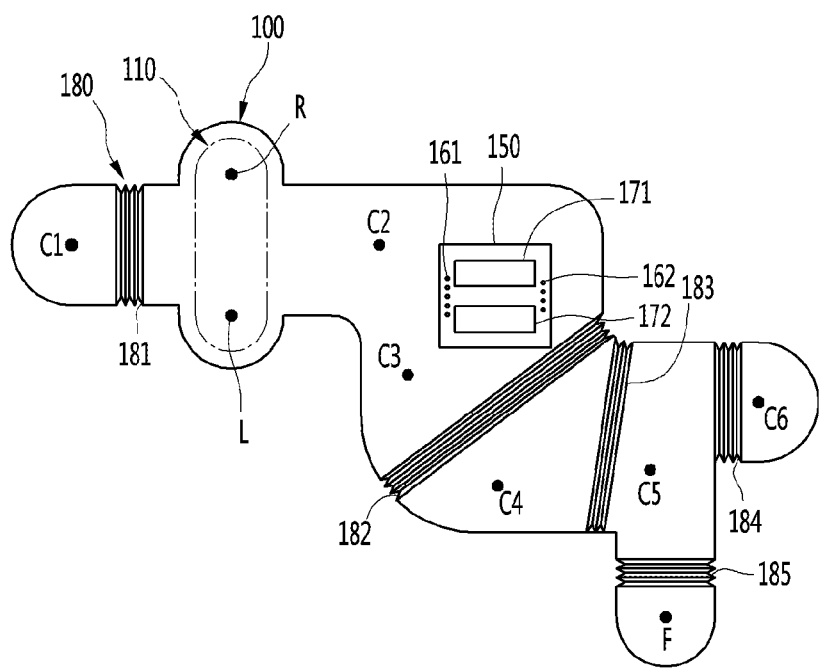
FIG. 3 is a view exemplarily illustrating a shape in which the patch portion includes a wrinkled portion according to one embodiment of the present invention.

FIG. 3 is a view exemplarily illustrating a shape in which the patch portion includes a wrinkled portion according to one embodiment of the present invention.

Meanwhile, as described above, the patch portion 100 may be manufactured to have various sizes while a human body is classified into large categories such as an adult, child, and the like.

Meanwhile, in order to be attached to the human body 5 which differs slightly even in the same category, the patch portion 100 may be formed to have flexibility and elasticity. That is, the patch portion 100 may be formed to have an elastic or flexible material.

Accordingly, the patch portion 100 has an advantage of being precisely matched with the above-described electrode position even when the patch portion having the same size is attached to the human body 5 having a size within a certain range.

Meanwhile, the patch portion 100 may further include a wrinkled portion 180 located between the electrodes.

The wrinkled portion 180 may increase or decrease the size of the patch portion 100.

In detail, the wrinkled portion 180 may be formed so that one surface of the patch portion 100 may be folded or unfolded. As an example, when the wrinkled portion 180 is folded, there may be provided a wrinkled shape. Also, when the wrinkled portion 180 is completely unfolded, there may be provided a flat surface.

The wrinkled portion 180 may be formed between at least one electrode and another electrode of the plurality of electrodes C1 to C6, R, L, and F. Also, the wrinkled portion 180 may be formed to be folded a plurality of times to decrease a size of a corresponding position or to be unfolded a plurality of times to increase the size.

That is, the wrinkled portion 180 may be formed to be a foldable shape to be folded or unfolded a plurality of times. As an example, in some regions of the patch portion 100 which are included in the wrinkled portion 180, top surfaces and corresponding bottom surfaces respectively come into contact with each other to be folded.

Accordingly, the wrinkled portion 180 may be provided to be folded or unfolded to be matched with a variety of sizes of the human body 5. Consequently, the wrinkled portion 180 may increase flexibility or elasticity of the patch portion 100.

Accordingly, there is an advantage of precisely attaching the electrodes of the patch portion 100 to the electrode positions adequate for a size of the human body 5 by using a single patch portion 100 regardless of the size of the human body 5 to which the patch portion 100 is attached.

Also, since it is unnecessary to manufacture the patch portion 100 for each of a variety of sizes, economical efficiency and productivity of the wireless electrocardiogram monitoring device 10 may be improved.

A plurality of such wrinkled portions 180 may be provided. As an example, the wrinkled portion 180 may include a first wrinkled portion 181 formed between the first electrode C1 and the second electrode C2, a second wrinkled portion 182 formed between the third electrode C3 and the fourth electrode C4, a third wrinkled portion 183 formed between the fourth electrode C4 and the fifth electrode C5, a fourth wrinkled portion 184 formed between the fifth electrode C5 and the sixth electrode C6, and a fifth wrinkled portion 185 formed between the sixth electrode C6 and the furcating electrode F.

The first wrinkled portion 181 may increase or decrease a distance h2 between the first electrode C1 and the second electrode C2. The first wrinkled portion 181 may be located to cross a space between the first electrode C1 and the second electrode C2 in a width direction of the patch portion 100.

Accordingly, the first electrode C1 and the second electrode C2 may be attached to be matched with the first and second electrode positions V1 and V2, respectively, which slightly vary for each size of the human body 5.

The above description of the first wrinkled portion 181 may also be used as a description of the second wrinkled portion 182 to the fifth wrinkled portion 185.

Also, the second wrinkled portion 182 may be located to cross a space between the fourth electrode C4, the fifth electrode C5, and the sixth electrode C6 and the third electrode C3 in a width direction.

However, the wrinkled portion 180 may be formed between the second electrode C2 and the third electrode C3 or between the right electrode R and the left electrode L.

Figure 4:
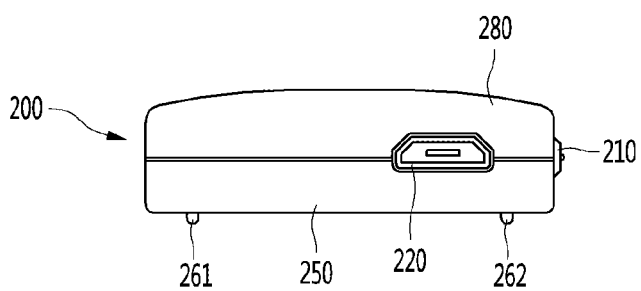
FIG. 4 is a view illustrating a top of a module portion according to one embodiment of the present invention.
Figure 5:
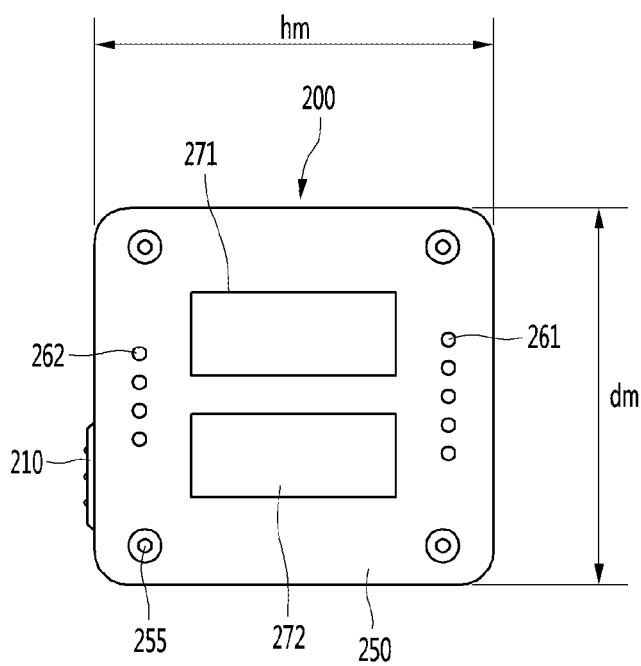
FIG. 5 is a view illustrating a bottom of the module portion according to one embodiment of the present invention.
Figure 6:
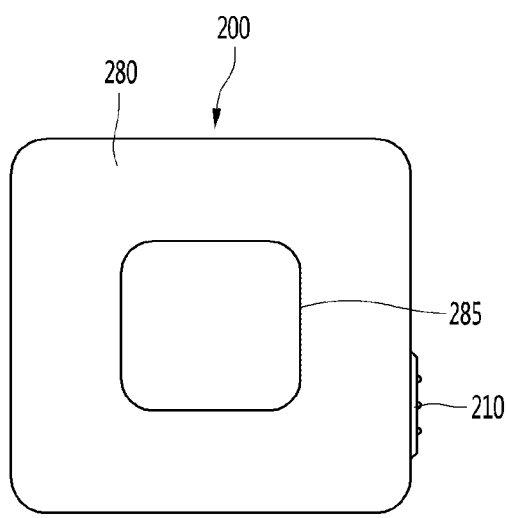
FIG. 6 is a side view illustrating the module portion according to one embodiment of the present invention.

FIG. 4 is a view illustrating the top of the module portion according to one embodiment of the present invention, FIG. 5 is a view illustrating the bottom of the module portion according to one embodiment of the present invention, and FIG. 6 is a side view illustrating the module portion according to one embodiment of the present invention.

Referring to FIGS. 4 to 6, the module portion 200 may include a bottom portion 250 coupled to the module mounting portion 150 and a top portion 280 coupled to a top of the bottom portion 250.

The bottom portion 250 and the top portion 280 may be coupled to each other to form an internal space. As an example, the bottom portion 250 and the top portion 280 may be coupled to each other using a fixing screw 255.

In the internal space of the module portion 200, a communication module capable of performing wireless communication, a central processing module capable of processing information sensed by the plurality of electrodes, a memory module capable of storing information, and a battery configured to provide power may be electrically connected to one another.

Accordingly, the module portion 200 may process, measure, store, transmit, and display the electrocardiograms of the twelve channels from values sensed by the plurality of electrodes.

The communication module included in the module portion 200 may be provided to perform a wireless communication method such as WiFi, Bluetooth, and the like.

Meanwhile, the module portion 200 may receive, treat or process, and transmit electrical signals from the plurality of electrodes to a smart device 300 which will be described below.

The module portion 200 may further include the module magnets 271 and 272 configured to guide coupling with the module mounting portion 150.

The module magnets 271 and 272 may be located at a central part of the bottom portion 250. In detail, the module magnets 271 may include a first module magnet 271 coupled to the first magnet 171 and a second module magnet 272 coupled to the second magnet 172.

That is, the first module magnet 271 and the second module magnet 272 may be located to correspond to the first magnet 271 and the second magnet 272, respectively.

Accordingly, the second module magnet 272 may be located to be spaced downward at a certain interval apart from the first module magnet 271.

The module portion 200 may further include module electrical connection devices 261 and 262 which come into contact with the pogo-pins 161 and 162 of the module mounting portion 160.

The module electrical connection devices 261 and 262 may include pogo-pins. Accordingly, the module electrical connection devices 261 and 262 may be referred to as module pogo-pins 261 and 262. Hereinafter, a case in which the module electrical connection devices 261 and 262 are provided as pogo-pins will be described as a reference.

The module pogo-pins 261 and 262 may include a first module pogo-pin 261 which comes into contact with and is electrically connected to the first pogo-pin 161 and a second module pogo-pin 262 which comes into contact with and is electrically connected to the second pogo-pin 162.

That is, the first module pogo-pin 261 may protrude downward from the bottom portion 250 to correspond to the first pogo-pin 161. Likewise, the second module pogo-pin 271 may protrude downward from the bottom portion 260 to correspond to the second pogo-pin 162.

The number of such first module pogo-pins 261 may correspond to the number of such first pogo-pins 161. As an example, the first module pogo-pins 261 may include five pogo-pins arranged to be in a row.

The number of such second module pogo-pins 262 may correspond to the number of such second pogo-pins 162. As an example, the second module pogo-pins 262 may include four pogo-pins arranged to be in a row.

Accordingly, information sensed by the plurality of electrodes may be received at the module portion 200.

The bottom portion 250 of the module portion 200 may have a size corresponding to the module mounting portion 150. As an example, a width hm of the bottom portion 250 may be 35 mm and a length dm of the bottom portion 250 may be 33 mm.

Also, the module portion 200 may further include a universal serial bus (USB) portion 220 configured to change a battery therein, a display 285 configured to process and display the information sensed by the plurality of electrodes to a user, and a switch 210 configured to turn on or off power.

The USB port 220 may be provided on one side surface of the module portion 200. Accordingly, the user may separate the module portion 200 from the module mounting portion 150 to charge the battery and may connect a power source thereto using the USB port 220 through wires.

The switch 210 may be provided as a slidable type, a button type, and the like. As an example, the switch 210 may be provided as a slidable switch configured to be slidably movable on an outer surface of the module portion 200.

The switch 210 may be provided on one side surface of the module portion 200. Also, the display 285 may be formed on the top portion 280 of the module portion 200.

FIG. 7 is a longitudinal cross-sectional view exemplarily illustrating a structure of the wireless electrocardiogram monitoring device according to one embodiment of the present invention.

As described above, the patch portion 100 may include the bottom surface detachably attached to the chest of the human body 5 and the top surface exposed outward. Also, as described above, the patch portion 100 may include a plurality of electrodes which are attachable to the human body 5.

Among the plurality of electrodes, the first to sixth electrodes C1 to C6 and the furcating electrode F may be formed on the bottom surface of the patch portion 100. Also, the right electrode R and the left electrode L may be formed on the top surface of the patch portion 100.

The top surface of the patch portion 100 may be understood as other surfaces excluding a surface detachably attached to the human body 5. Accordingly, the top surface of the patch portion 100 may be referred to as an outer surface of the patch portion 100. On the other hand, since the bottom surface of the patch portion 100 is detachably attached to the human body 5, the bottom surface may be referred to as an inner surface of the patch portion 100.

The first to sixth electrodes C1 to C6 and the furcating electrode F may include components, a structure, and a connection relation of a downward patch portion 130 which will be described below. Also, the right electrode R and the left electrode L may include components, a structure, and a connection relation of an upward patch portion 110 which will be described below.

In other words, the upward patch portion 110 includes the right electrode R and the left electrode L. Also, the downward patch portion 130 includes the first to sixth electrodes C1 to C6 and the furcating electrode F.

That is, the components, structure, and connection relations, and the like of the downward patch portion 130, which will be described below in detail, will also be used as each of the first to sixth electrodes C1 to C6 and the furcating electrode F.

Likewise, the components, structure, and connection relation, and the like of the upward patch portion 110 may also be used as each of the right electrode R and the left electrode L.

Referring to FIG. 7, the patch portion 100 may include the downward patch portion 130 which is the bottom surface attached to the human body 5 and provided to expose some of the plurality of electrodes and the upward patch portion 110 which is an outer surface exposed outward and provided to expose other of the plurality of electrodes.

The upward patch portion 110 may be provided to allow both hands or both fingers of the human body 5 to come into contact therewith, and the downward patch portion 130 may be provided to be attached to the chest of the human body 5.

That is, the electrodes provided on the upward patch portion 110 may be disposed to face a direction opposite to the electrodes provided on the downward patch portion 130.

Also, since the electrodes provided on the upward patch portion 110 are provided on one sheet or patch with the electrodes provided on the downward patch portion 130, a signal provided from the hand or finger of the human body 5 has an advantage of being obtained by the integrated patch portion 100 detachably attached to the chest.

Also, the patch portion 100 may further include an upward printed circuit 115 configured to connect the upward patch portion 110 to the pogo-pins 161 and 162 of the module mounting portion 150 and a downward printed circuit 117 configured to connect the downward patch portion 115 to the pogo-pins 161 and 162 of the module mounting portion 150.

On the basis of FIG. 7, the upward patch portion 110 may be formed on the outer surface of the patch portion 100. Also, the downward patch portion 130 may be formed on the bottom surface of the patch portion 100.

Meanwhile, the module mounting portion 150 may be formed on the top surface of the patch portion 100. Accordingly, the module portion 200 may be coupled to the top surface of the patch portion 100 like the upward patch portion 110.

The upward patch portion 110 may include an upward contact portion 125 formed on the top surface of the patch portion 100 to be exposed and an upward electrode portion 111 electrically connected to the upward contact portion 125.

The upward contact portion 125 may be formed of an electrolyte gel adequate for skin contact. Also, the upward contact portion 125 may be formed of a material having electrical conductivity. As an example, the upward contact portion 125 may include a hydrogel.

The upward contact portion 125 may be formed to protrude upward from the top surface of the patch portion 100. Also, the upward contact portion 125 may be formed to have a variety of shapes to be easily touched by the hand of the user.

As an example, the upward contact portion 125 may be formed to have a protrusion structure protruding upward to be stably touched or gripped by the hand of the user. Also, the upward contact portion 125 may be formed to have a thimble shape to allow the finger to be easily inserted thereinto.

The upward electrode portion 111 may be located below the upward contact portion 125. As an example, the upward electrode portion 111 may be formed to extend downward from the upward contact portion 125.

The right electrode R and the left electrode L which have been described above may be understood as components of the upward electrode portion 111.

The upward electrode portion 111 may be formed to be inserted into or fixed to the patch portion 110.

Also, the upward electrode portion 111 may be electrically connected to the upward contact portion 125.

The upward electrode portion 111 may be connected to the pogo-pins 161 and 162 through the upward printed circuit 115 formed in the patch portion 100. As an example, the upward printed circuit 115 may extend downward from the upward electrode portion 111 and be connected to the first pogo-pin 161.

However, the upward printed circuit 115 may be formed as a wire.

Accordingly, information sensed by the upward contact portion 125 which comes into contact with the left hand or right hand of the user may be transmitted to the module portion 200 through the upward electrode portion 111, the upward printed circuit 115, the first pogo-pin 161, and the first module pogo-pin 261 which are electrically connected.

Also, the upward patch portion 110 may further include an upward adhesive portion 123 which is attachable to the hand of the user.

The upward adhesive portion 123 may be formed of a material which is adhesive to the skin. As an example, the upward adhesive portion 123 may include an adhesive tape.

The upward adhesive portion 123 may be located on the outer surface on which the upward contact portion 125 is located. Accordingly, the upward adhesive portion 123 may be exposed in an outward direction with the upward contact portion 125.

Also, the upward adhesive portions 123 may be located while being spaced at a certain interval apart bidirectionally on the basis of the upward contact portion 125.

The upward adhesive portion 123 is attached to the hand, a part of the hand, the finger, or a finger tip and may be formed to have a relative small size unlike a downward adhesive portion 131 of the downward patch portion 130 which will be described below.

The upward adhesive portion 123 may be attached to the hand or finger to maintain a stable contact between the upward contact portion 125 and the hand or finger. Accordingly, since the upward patch portion 110 may be attached to the hand or finger of the user, it is possible to stably transmit a signal.

The downward patch portion 130 may include a downward adhesive portion 131 and a downward contact portion 132 which are formed on the bottom surface of the patch portion 100 to be exposed and a downward electrode portion 133 electrically connected to the downward contact portion 132.

The downward adhesive portion 131 may be detachably attached to the chest of the human body 5. The downward adhesive portion 131 may be attached to a part near the chest of the human body 5 to stably maintain a contact between the downward contact portion 132 and the human body 5.

The downward adhesive portion 131 may be formed to occupy a majority of an area of the bottom surface of the patch portion 100. Also, the downward adhesive portion 131 may be formed to have a relatively larger area than the upward adhesive portion 123.

However, the downward adhesive portion 131 may be located to be coplanar with the downward contact portion 132. That is, the downward adhesive portion 131 may be formed to surround the downward contact portion 132. Accordingly, one part of the bottom surface of the patch portion 100 may be formed to be the downward contact portion 132.

The downward adhesive portion 131 may be formed of a material which is adhesive to the skin. As an example, the downward adhesive portion 131 may include an adhesive tape.

The downward contact portion 132 may be formed of an electrolyte gel adequate for skin contact. Also, the downward contact portion 132 may be formed of a material having electrical conductivity. As an example, the downward contact portion 132 may include a hydrogel.

The downward contact portion 132 may come into contact with the above-described first to sixth electrode positions V1 to V6 of the human body 5.

The downward electrode portion 133 may be located above the downward contact portion 132. As an example, the downward electrode portion 133 may be formed to extend upward from the downward contact portion 132.

The above-described first to sixth electrodes C1 to C6 and the furcating electrode F may be understood as components of the downward electrode portion 133.

The downward electrode portion 133 may be formed to be inserted into or fixed to the patch portion 110.

Also, the downward electrode portion 133 may be electrically connected to the downward contact portion 132.

The downward electrode portion 133 may be connected to the pogo-pins 161 and 162 through the downward printed circuit 117 formed in the patch portion 100. As an example, the downward printed circuit 117 may extend upward from the downward electrode portion 133 and be connected to the second pogo-pin 162.

However, the downward printed circuit 117 may be formed as a wire.

Accordingly, information sensed at the first to sixth electrode positions V1 to V6 of the human body 5 of the user and the downward contact portion 132 which comes into contact with the skin between the fourth electrode position V4 and the left leg may be transmitted to the module portion 200 through the downward electrode portion 133, the downward printed circuit 117, the pogo-pins 161 and 162, and the module pogo-pins 271 and 272 which are electrically connected.

According to the above-described patch portion 100 according to the embodiment of the present invention, voltage (or current) information generated by cardiac action may be detected by the upward patch portion 110 from both hands or the finger. Accordingly, there is an advantage of obtaining more stable, accurate, and reliable electrocardiogram signal information than when conventional signal information detected at a shoulder or an upper arm is unstable and has weak strength or intensity so that amplification and filtering for measuring electrocardiograms are essentially necessary.

Meanwhile, a case in which the user cannot autonomously move his or her arm and hand to touch the upward contact portion 125 such as a person losing his or her consciousness or having difficulty in moving his or her arms may occur. To this end, the upward patch portion 100 may be formed to be a detachably attachable component.

Accordingly, an assistant may attach a separable component (finger patch) of the upward patch portion 100 to the hand or finger of the user having difficulty in moving his or her arms and then may move and couple the hand or finger of the user to a fixing portion of the upward patch portion 100 fixed to the top surface of the patch portion 100 so as to measure electrocardiograms.

That is, the upward patch portion 110 may include the fixing portion inserted into or fixed to the top surface of the patch portion 100 and a finger patch 120 provided to be detachably attachable to the fixing portion.

The finger patch 120 may be a separation portion of the upward patch portion 110.

The fixing portion of the upward patch portion 110 includes the above-described upward electrode portion 111. Also, the upward electrode portion 111 may be formed to be fixed to an inside of the patch portion 100.

Also, the fixing portion of the upward patch portion 110 may further include an upward installation portion 112 configured to guide attachment and detachment with the finger patch 120.

The upward installation portion 112 may provide a coupling force to the finger patch 120.

Also, the upward installation portion 112 may be formed to surround the upward electrode portion 111. As an example, the upward electrode portion 111 may be formed as a circular electrode, and the upward installation portion 112 may be formed to have a donut shape to allow the upward electrode portion 111 to be inserted into a center thereof. That is, the upward installation portion 112 may be formed to extend radially along an outer diameter of the upward electrode portion 111.

The upward installation portion 112 may be formed of a variety of materials according to a method of coupling with the finger patch 120. As an example, the upward installation portion 112 may include a Velcro type, a magnet type, and a snap-button type.

That is, in the upward patch portion 110, the fixing portion and the separation portion 120 may be provided to be detachably attachable to each other using the Velcro type, the magnet type, or the snap-button type.

The finger patch 120 may include the upward contact portion 125 and the upward adhesive portion 123 which have been described above.

That is, the upward contact portion 125 and the upward adhesive portion 123 may be provided to be separable from the upward electrode portion 111.

Also, the finger patch 120 may further include an upward electrode guide 121 connected to a bottom of the upward contact portion 125 and configured to guide electrical connection with the upward electrode portion 111 and an upward installation guide 122 detachably attached to the upward installation portion 112.

The upward electrode guide 121 may be formed of the same material as that of the upward electrode portion 111. Also, the upward electrode guide 121 may be formed to extend from the upward contact portion 125 toward the bottom surface of the finger patch 120.

Also, the upward electrode guide 121 may be formed at a position corresponding to the upward electrode portion 111. Accordingly, when the finger patch 120 is fixed to the fixing portion, the upward electrode guide 121 may come into contact with and be electrically connected to the upward electrode portion 111.

The upward installation guide 122 may be formed on the bottom surface of the finger patch 120.

Also, the upward installation guide 122 may be formed to be detachably attachable to the upward installation portion 122. Accordingly, the upward installation guide 122 may be formed to correspond to the upward installation portion 122. As an example, the upward installation guide 122 may be formed to surround the upward electrode guide 121.

Also, as described above, the upward installation guide 122 and the upward installation portion 122 may be provided as a Velcro type, a magnet type, or a snap-button type. Also, the upward installation guide 122 and the upward installation portion 122 may be formed as one pair to correspond to each other.

Hereinafter, the upward installation portion 112 will be described on the basis of a case in which the upward installation portion is provided as the magnet type to be detachably attachable to the finger patch 120.

Figure 8:
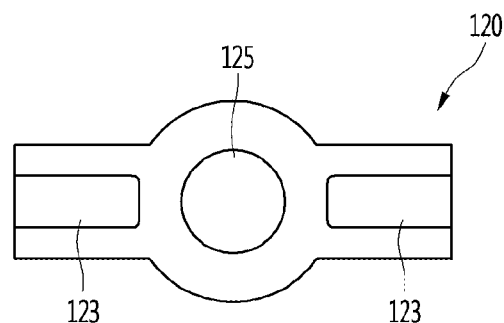
FIG. 8 is a plan view illustrating a finger patch according to one embodiment of the present invention.
Figure 9:
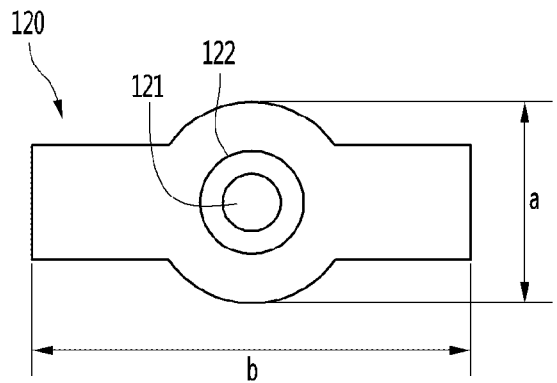
FIG. 9 is a bottom view illustrating the finger patch according to one embodiment of the present invention.

FIG. 8 is a plan view illustrating the finger patch according to one embodiment of the present invention, and FIG. 9 is a bottom view illustrating the finger patch according to one embodiment of the present invention.

Referring to FIGS. 8 and 9, the finger patch 120 may include the upward adhesive portion 123 and the upward contact portion 125 which are formed on a top surface to be exposed.

Also, the finger patch 120 may include the upward installation guide 122 and the upward electrode guide 121 which are formed on the bottom surface to come into contact with the fixing portion of the upward patch portion 110.

On the basis of the upward contact portion 125, the upward adhesive portions 123 may extend from positions spaced at a certain interval apart bidirectionally from the upward contact portion 125.

The finger patch 120 may include a variety of shapes. As an example, the finger patch 120 may be formed to have an exterior having a watch shape overall. Here, a length b of the finger patch 120 may be formed to be about 40 mm, and a width a of the finger patch 120 may be formed to be about 10 mm. Accordingly, the finger patch 120 may be attached to surround the finger.

Also, the upward electrode guide 121 connected to a bottom of the upward contact portion 125 may be formed to have a circular shape.

The upward installation guide 122 may be formed to surround the upward electrode guide 121. As an example, the upward installation guide 122 coupled to the upward installation portion 112 may be formed to have a donut shape around the upward electrode guide 121.

Figure 10:
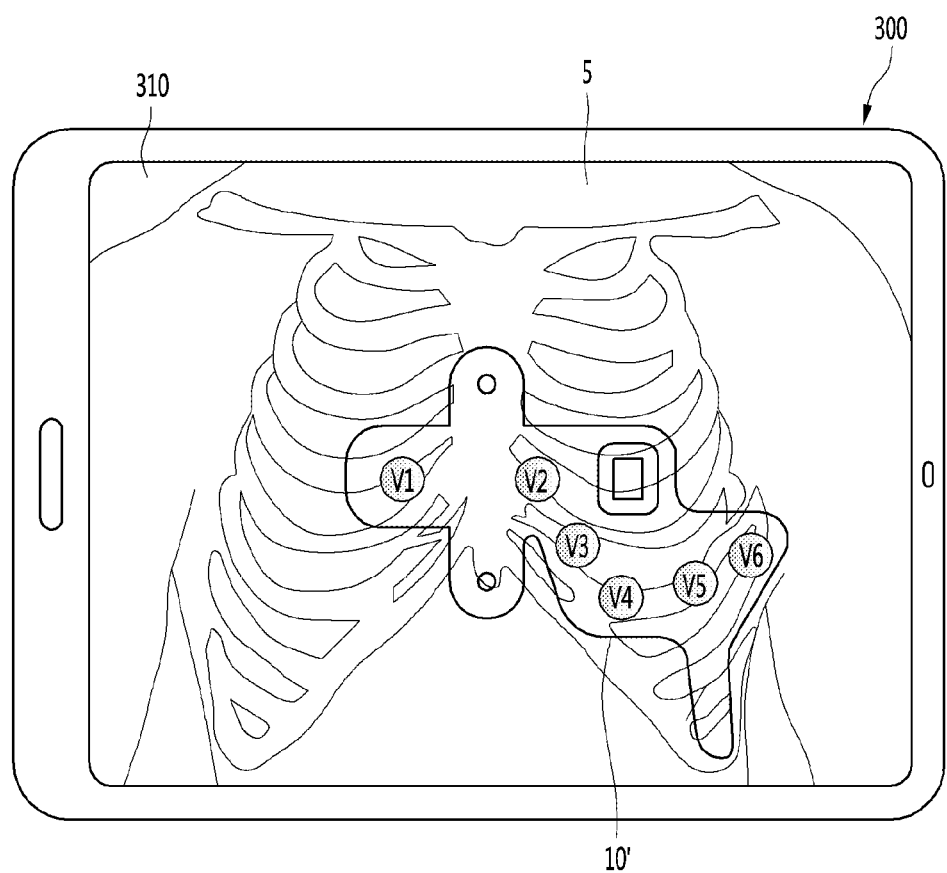
FIG. 10 is a view illustrating an example of using a smart device configured to guide installation of the wireless electrocardiogram monitoring device according to one embodiment of the present invention.

FIG. 10 is a view illustrating an example of using a smart device configured to guide installation of the wireless electrocardiogram monitoring device according to one embodiment of the present invention.

Referring to FIG. 10, the wireless electrocardiogram monitoring device 10 may further include a smart device 300 configured to guide nine electrodes to be attached to precise positions of the human body 5.

The smart device 300 may include an electronic device including a display, a camera, and a wireless communication module. As an example, the smart device 300 may include a smart phone, a tablet PC, a portable imaging device, and the like.

The smart device 300 may transmit and receive information through communication with the module portion 200. As an example, the smart device 300 may receive size information of the patch portion 100 attached to the user from the module portion 200. The smart device 300 may include a screen portion 310 configured to provide an image captured by the included camera.

Also, the smart device 300 may guide an installation position of the wireless electrocardiogram monitoring device 10 on a captured image of the human body 5 through the screen portion 310. As an example, the smart device 300 may guide the user through a precise installation position of the wireless electrocardiogram monitoring device 10 using augmented reality.

In detail, the smart device 300 may guide an installation position of the patch portion 100 on the human body 5 of the user displayed on the screen portion 310 using an augmented screen 10' by reflecting the size information of the wireless electrocardiogram monitoring device 10 transmitted from the module portion 200.

Accordingly, the user may easily and precisely attach the wireless electrocardiogram monitoring device 10 at the above-described first to sixth electrode positions V1 to V6 using the smart device 300 at home without a professional help.

FIGS. 11 and 12 illustrate, as still another embodiment of the present invention, an example in which some of upward electrodes, for example, the right electrode R and the left electrode L are mounted on the module 200.

In this case, the right electrode R and the left electrode L have no connection with the patch portion 100 and are directly connected to a circuit portion of the module 200.

Accordingly, since a sum of the first and second pogo-pins 161 and 162, which is nine, only needs to be 7 and there are no upward electrodes, a thickness of the patch portion 100 decreases.

Meanwhile, the module 200 may include an individual recognition function such as a fingerprint recognition.

DESCRIPTION OF REFERENCE NUMERALS

10: wireless electrocardiogram monitoring device
100: patch portion
200: module portion
300: smart device

The invention claimed is:

1. A wireless electrocardiogram monitoring device comprising:
a patch including:
a bottom surface attachable to a human body;
a top surface positioned opposite the bottom surface;
a downward patch portion comprising at least seven electrodes exposed through the bottom surface;
an upward patch portion comprising a fixing portion, a first finger patch, and a second finger patch, the fixing portion comprising a first electrode electrically connected to the first finger patch and a second electrode electrically connected to the second finger patch, the first electrode and the second electrode being exposed through the top surface, and each of the first and second finger patches detachably attached to the fixing portion and configured to be attachable to at least a part of a hand of the human body;
a wrinkled portion for adjusting distances between the at least seven electrodes; and
a module portion separably coupled to the patch for wireless communication.

2. The wireless electrocardiogram monitoring device of claim 1, wherein each of the first and second finger patches comprises an upward contact portion protruding upward away from the top surface; and
wherein the upward patch portion further comprises an upward electrode portion extending toward a bottom of the upward contact portion and electrically connected to the module portion, and
wherein the upward contact portion includes a hydrogel.

3. The wireless electrocardiogram monitoring device of claim 1, wherein each of the first and second finger patches comprises an upward contact portion protruding upward away from the top surface; and
wherein the upward patch portion further comprises an upward electrode portion extending toward a bottom of the upward contact portion and electrically connected to the module portion, and
wherein the upward contact portion has a protrusion structure protruding upward from the top surface and is electrically connected to the upward electrode portion.

4. The wireless electrocardiogram monitoring device of claim 1, further comprising a smart device for picturing the human body and determining the positions of the electrodes of the downward patch portion.

5. The wireless electrocardiogram monitoring device of claim 1, wherein the patch is sized and shaped so that a first number of the at least seven electrodes are on a first side of a line connecting the first electrode for the right hand of the human body and the second electrode for the left hand of the human body and so that a second number of the at least seven electrodes is on a second side of the line, the second side being opposite the first and each of the first number and the second number includes at least one of the seven electrodes.

6. The wireless electrocardiogram monitoring device of claim 5, wherein the line is generally aligned with a centerline of the human body, the first side corresponds to a right side of the human body, and the second side corresponds to a left side of the human body.

7. The wireless electrocardiogram monitoring device of claim 5, wherein the second number is one and the first number is six.

* * * * *